(12) United States Patent
Ninkov

(10) Patent No.: US 12,037,302 B1
(45) Date of Patent: Jul. 16, 2024

(54) COMPOUND FOR TREATMENT OF BACTERIAL INFECTIONS OF DIFFERENT ETIOLOGY IN HUMANS

(71) Applicant: Tesla Bioscience ad Banja Luka, Banja Luka (BA)

(72) Inventor: Dusan Ninkov, San Diego, CA (US)

(73) Assignee: TESLA BIOSCIENCE AD BANJA LUKA, Banja Luka (BA)

( * ) Notice: Subject to any disclaimer, the term of this patent is extended or adjusted under 35 U.S.C. 154(b) by 326 days.

(21) Appl. No.: 17/241,366

(22) Filed: Apr. 27, 2021

Related U.S. Application Data

(60) Provisional application No. 63/169,695, filed on Apr. 1, 2021.

(51) Int. Cl.
*A61P 31/04* (2006.01)
*C07C 205/06* (2006.01)

(52) U.S. Cl.
CPC ............ *C07C 205/06* (2013.01); *A61P 31/04* (2018.01)

(58) Field of Classification Search
CPC ................................ C07C 205/06; A61P 31/04
See application file for complete search history.

(56) References Cited

U.S. PATENT DOCUMENTS 6,921,539 B2   7/2005   Ninkov

*Primary Examiner* — Paul V Ward
(74) *Attorney, Agent, or Firm* — Suiter Swantz IP

(57) ABSTRACT

The invention relates to a novel compound manufactured with the procedure of synthesis of bouncing Carvacrol and Lidocaine into one stable compound. Use of the compound as an active compound/potent antimicrobial for the treatment of bacterial infections in humans caused by pathogens resistant to antibiotics, such as Methicillin-resistant *Staphylococcus aureus* (MRSA), *Streptococcus faecalis*, *Mycobacterium tuberculosis*, *Escherichia* spp. *E. coli*, *Salmonella* spp. *Pasteurella* spp., *Corynebacterium* spp., *Bacillus* spp., *Bacillus anthracis*, *Clostridium* spp., *Spherophorus* spp., *Candida* spp., *Trichophyton* spp., *Microsporum* spp., *Mycobacterium* spp., *Vibrio* spp., *Cryptosporidium* spp., *Microsporidia* spp., *Listeria monocytogenes*, *Lawsonia intracellularis*, *Treponema dysenteriae*, *Enterococcus* spp., *Haemophilus* spp., *Campylobacter* spp., *Chlamydia* spp., *Brucella* spp., and other pathogenic bacterial species.

4 Claims, 7 Drawing Sheets

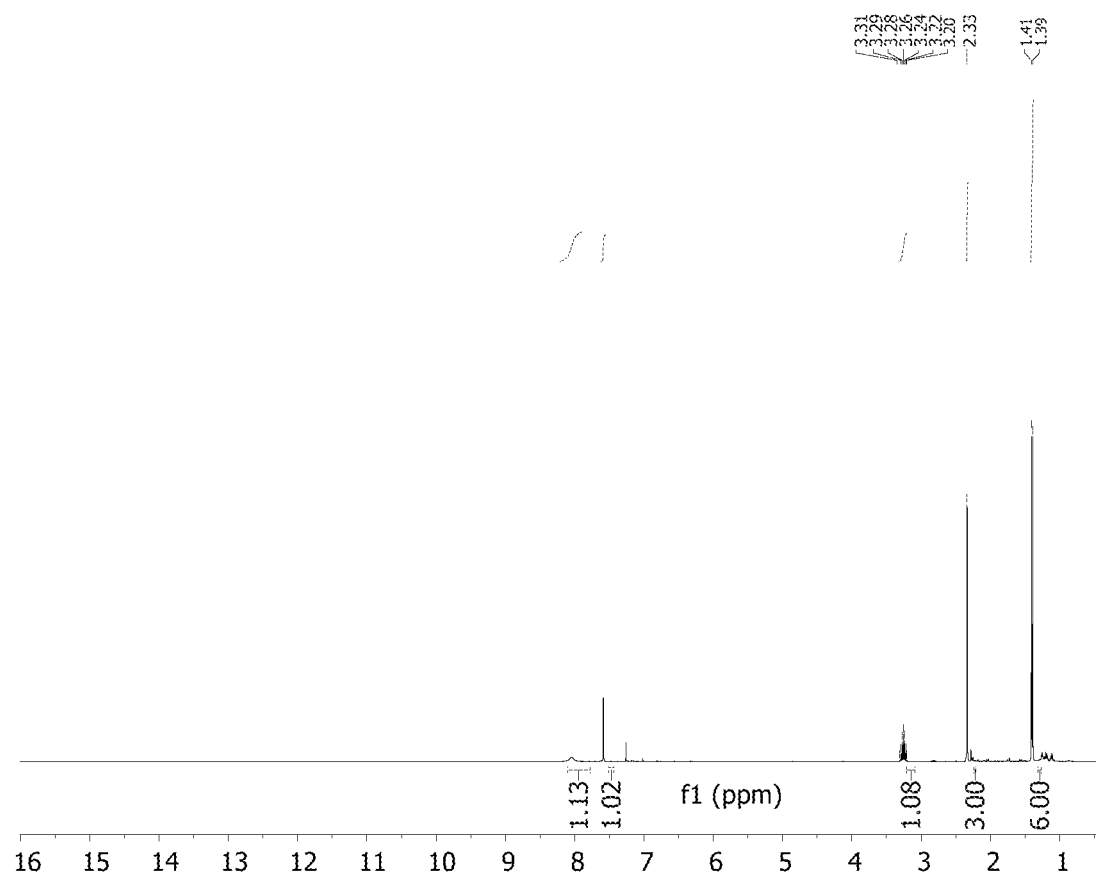
FIG. 1 1H-NMR spectrum of 2,4-dinitrocarvacrol

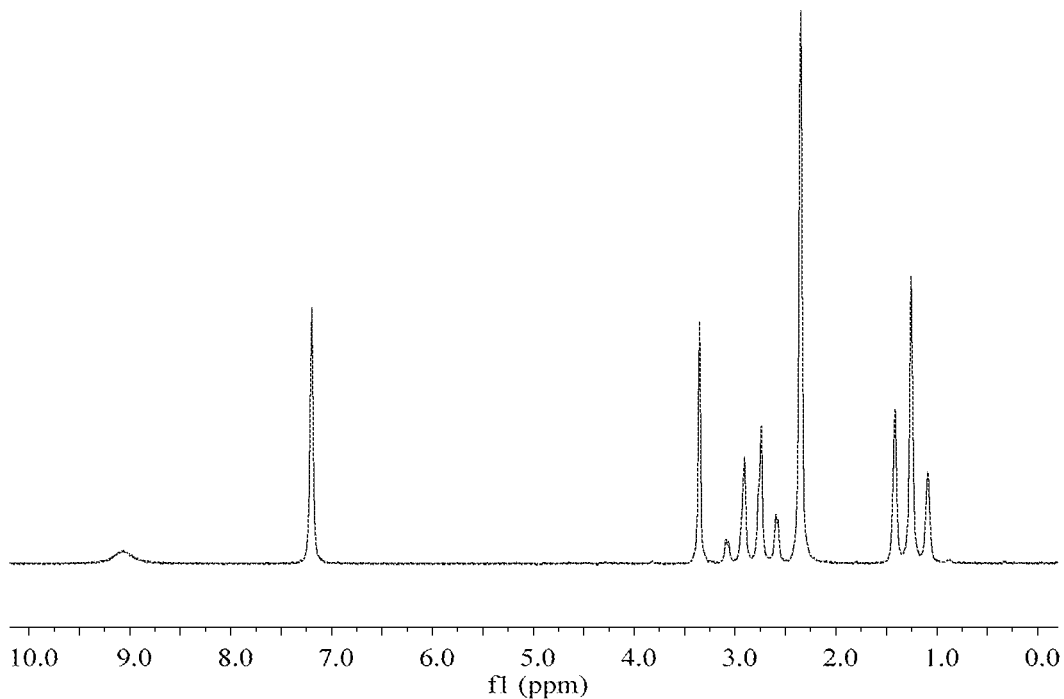
FIG. 2 1H-NMR spectrum of Lidocaine

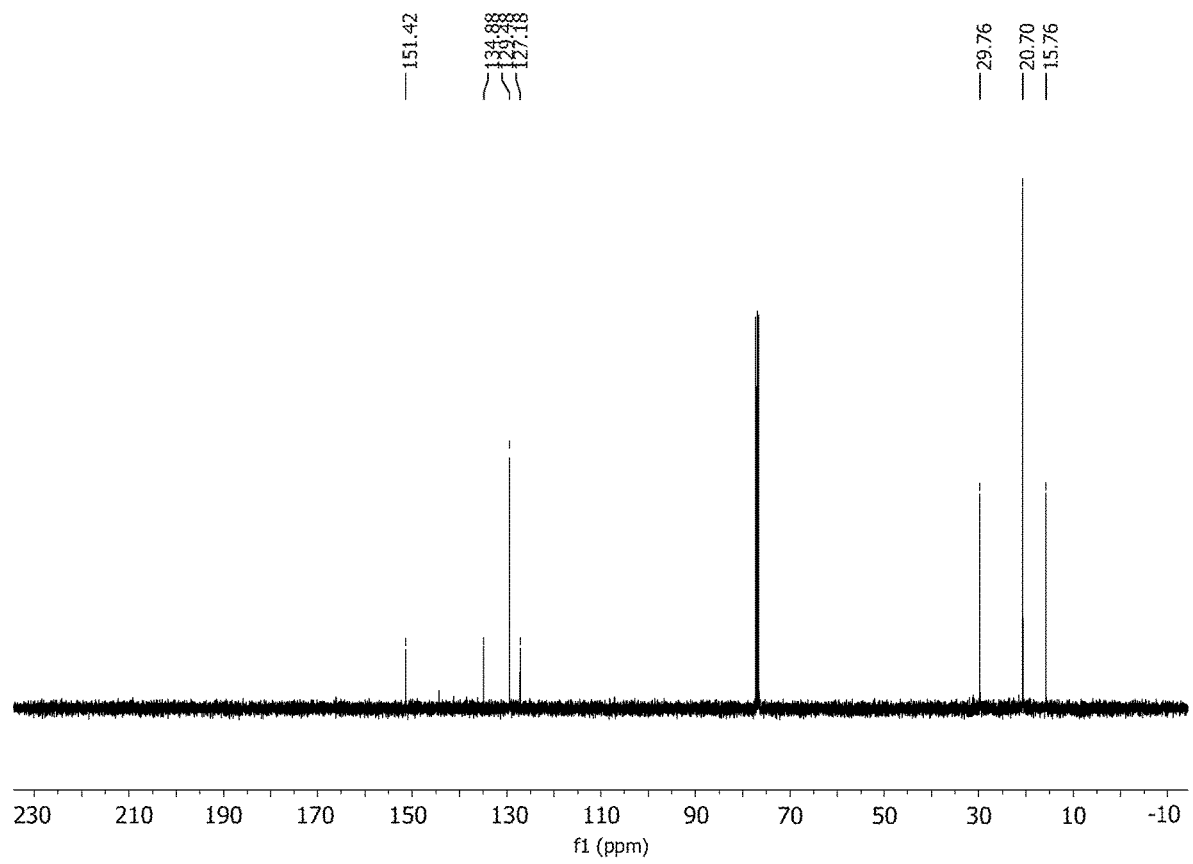
FIG. 3 13C-NMR spectrum of 2,4-dinitrocarvacrol

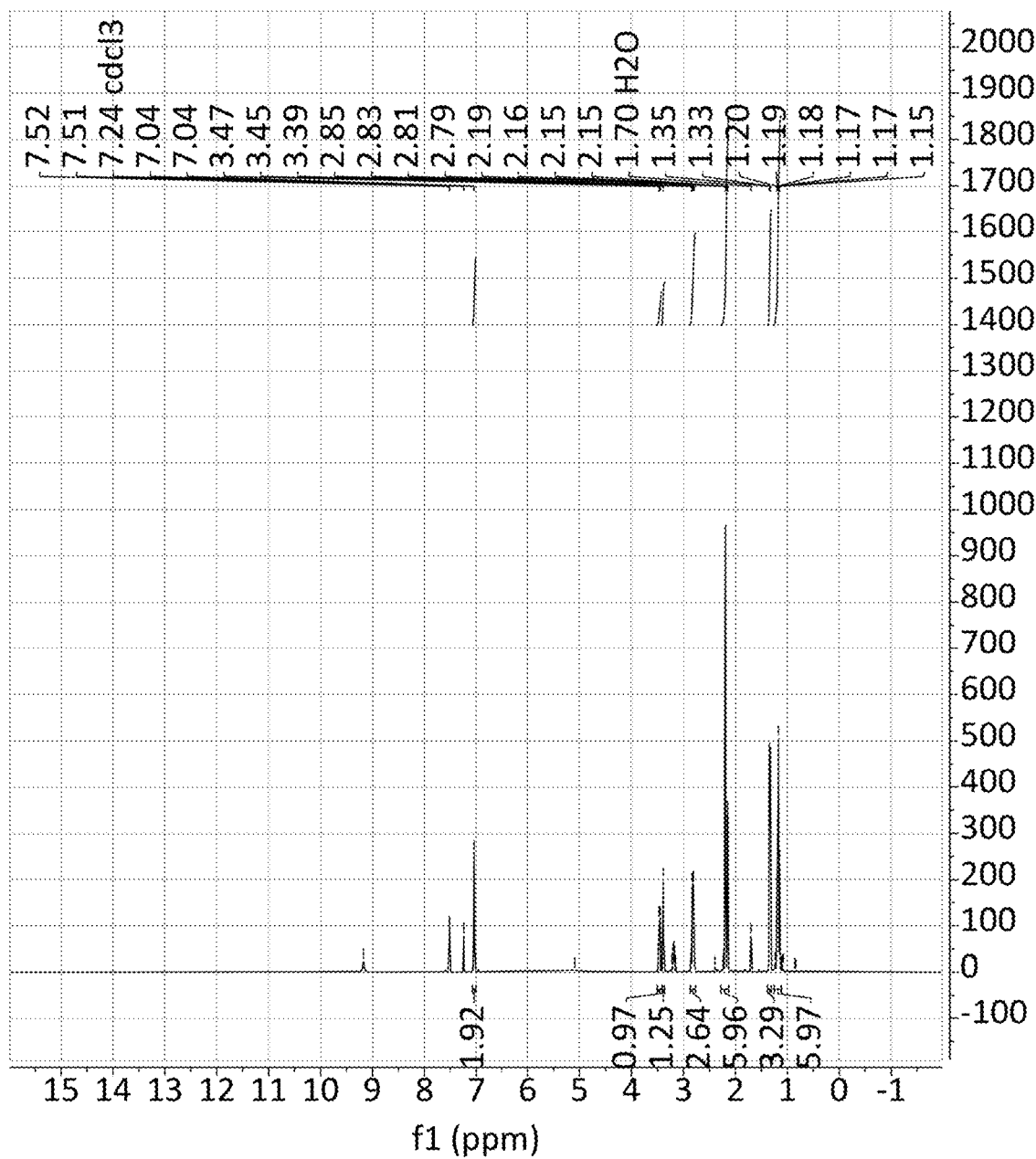
FIG. 4 1H-NMR spectrum of the novel compound

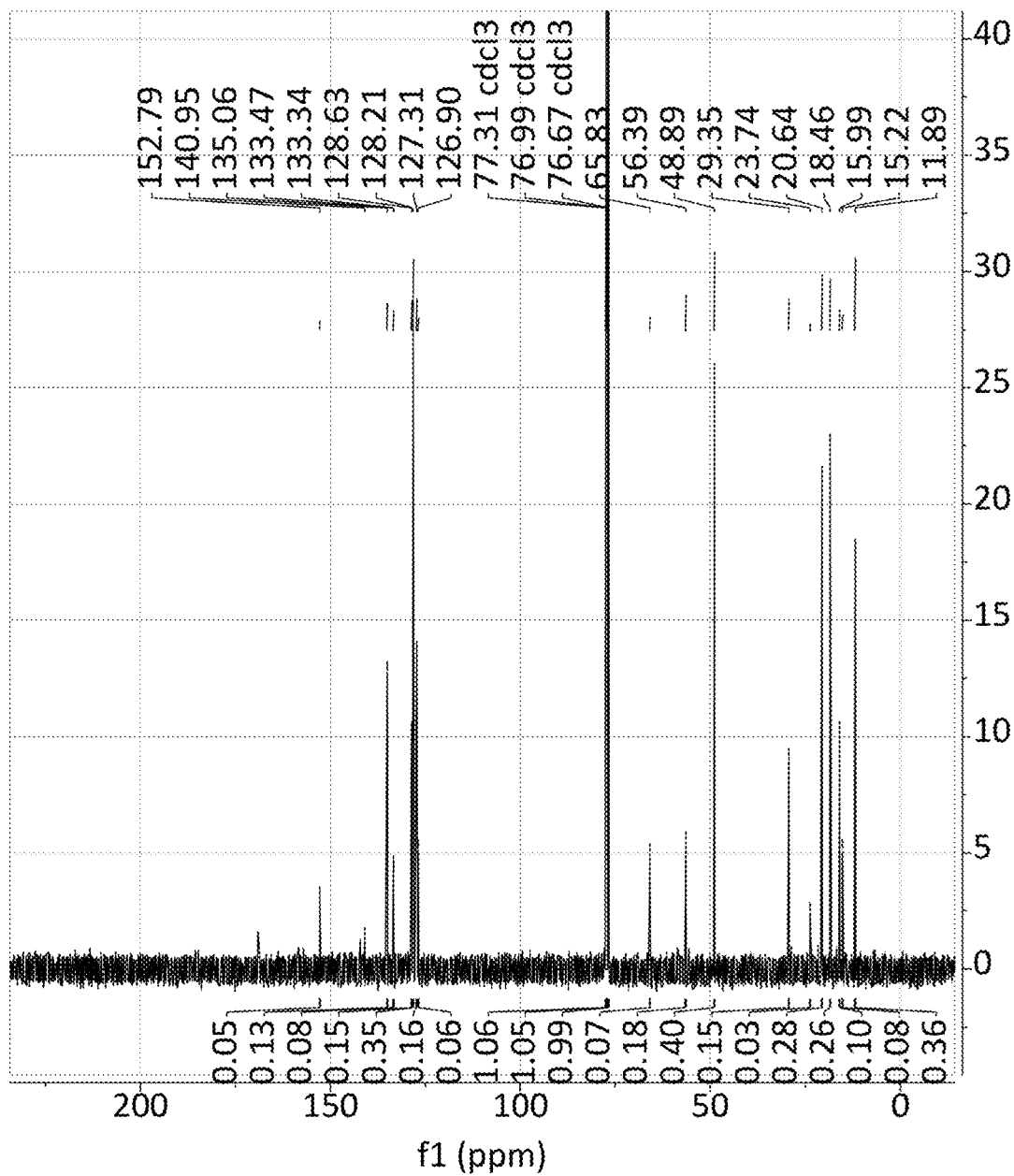
FIG. 5 13C-NMR spectrum of the novel compound

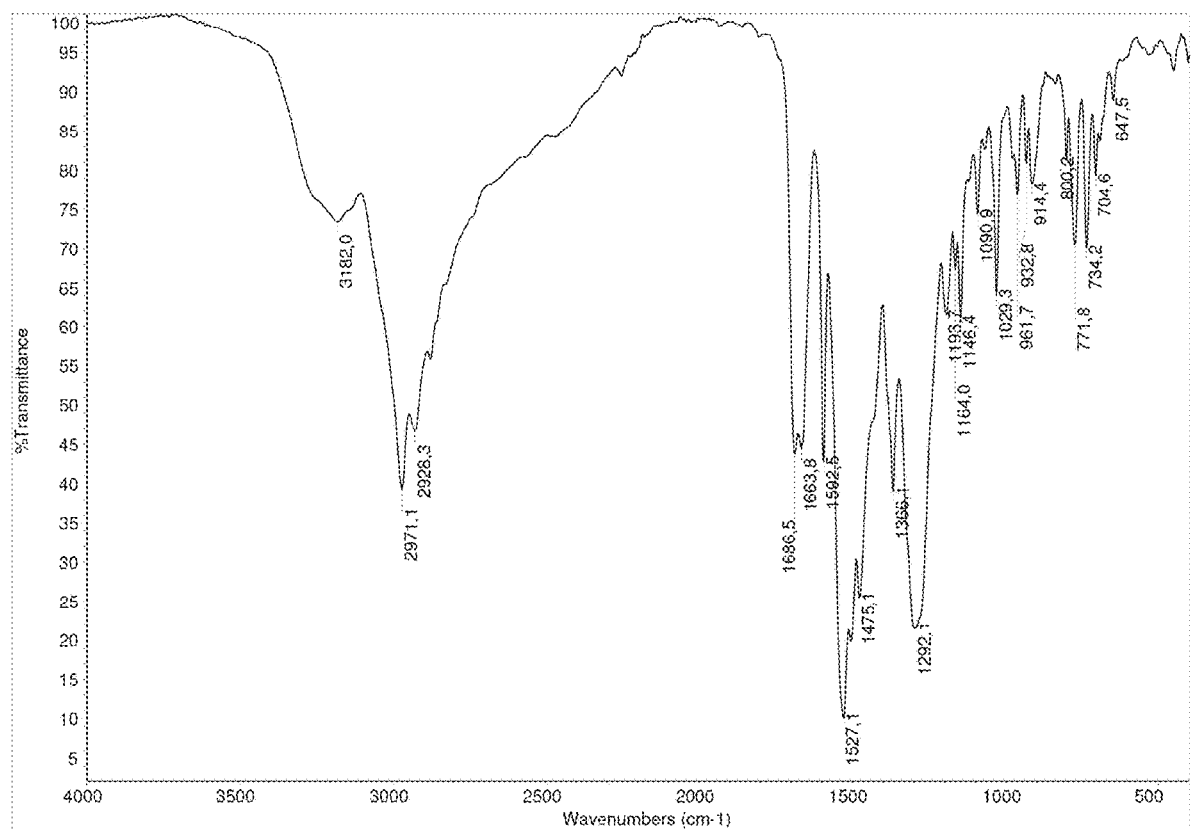
FIG. 6 IR spectrum of the novel compound

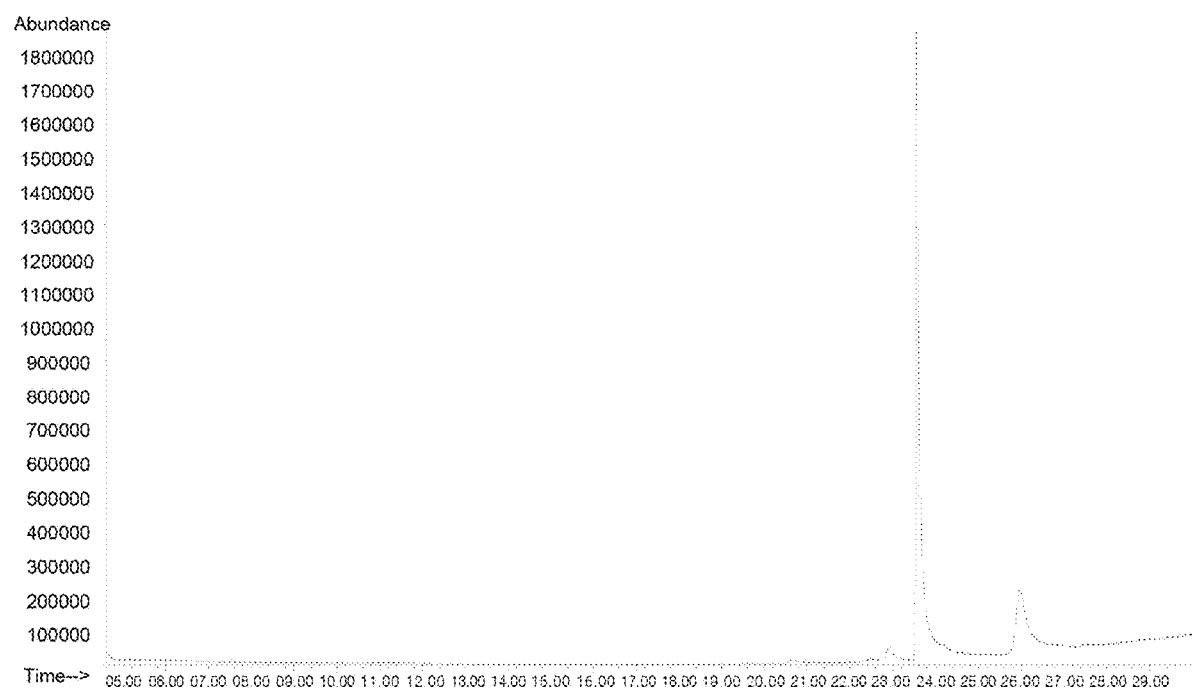
FIG. 7 Gas chromatography of the novel compound

COMPOUND FOR TREATMENT OF BACTERIAL INFECTIONS OF DIFFERENT ETIOLOGY IN HUMANS

FIELD OF THE INVENTION

The compound is a novel medicine created for the treatment of bacterial infections caused by resistant pathogens in humans.

BACKGROUND OF THE INVENTION

This invention is addresses the problems faced regarding bacterial infections in humans with the different etiology of pathogens. The compound is a broad-spectrum antimicrobial compound, in the form of a liquid meant for IV (Intravenous) therapy in order to treat said bacterial infections. The antimicrobial effect of Carvacrol is well known. This invention is completely novel because its main compounds, Carvacrol and Lidocaine, have been bounced into one stable compound by a special process of synthesis. The effect and uniqueness of this compound is the subject of this invention. The active principle of the compound is a stable quaternary ammonium complex of Carvacrol and Lidocaine. The compound is more effective than standard $3^{rd}$ generation cephalosporin antibiotics in the treatment of the mentioned infections. The compound is created to fight antibiotic resistant pathogenic bacteria, such as Methicillin-resistant *Staphylococcus aureus* (MRSA), *Streptococcus faecalis*, *Mycobacterium tuberculosis*, *Escherichia* spp. *E. coli*, *Salmonella* spp. *Pasteurella* spp., *Corynebacterium* spp., *Bacillus* spp., *Bacillus anthracis*, *Clostridium* spp., *Spherophorus* spp., *Candida* spp., *Trichophyton* spp., *Microsporum* spp., *Mycobacterium* spp., *Vibrio* spp., *Cryptosporidium* spp., *Microsporidia* spp., *Listeria monocytogenes*, *Lawsonia intracellularis*, *Treponema dysenteriae*, *Enterococcus* spp., *Haemophilus* spp., *Campylobacter* spp., *Chlamydia* spp., *Brucella* spp., and other pathogenic bacterial species. Based on the specific mechanism of action, the active compound of this invention is different from any other antibiotic currently available on the market. In this invention, an extra potent effect of the synergy of Carvacrol and Lidocaine is achieved. The antimicrobial efficiency of this novel compound will be significantly more effective than Carvacrol and Lidocaine by themselves or by their simple mixture.

Before the widespread use of Penicillin, infectious diseases were the leading cause of death among all age groups across the globe. Antibiotics have extended the lives and improved the quality of life of people since the early $20^{th}$ century. Many have thought that humanity was entering the post-pathogen era, where infectious disease was a historical footnote. Today, infective diseases are still the first leading cause of death and the leading cause of disability.

DESCRIPTION OF THE INVENTION

In the following text, the novelty and uniqueness of the compound will be elaborated.

Method of Production

The synthesis of our novel compound is achieved in a few steps. At first, a nitration of Carvacrol is used to make 2,4-dinitrocarvacrol, and after that trans-formation, an organic salt with free base Lidocaine is obtained. The nitration of Carvacrol is conducted at room temperature for a few hours in the presence of excess acetic anhydride with at least two equivalents of nitric acid. PLC plates are used to check the completion of the reaction. The reaction is violent, and care must be taken to avoid any accidents. In a mixture of Carvacrol and acetic anhydride in an ice bath with magnetic stirring, concentrated nitric acid (65%) dissolved in acetic anhydride is added one drop at a time. After about 6 h, the reaction is quenched by adding distilled water, allowing the product to separate from its acid constituents. The product is of a dark red color and needs to be washed with water until the acetic acid is removed from the mixture, with the absence of acetic acid's odor being a good indicator of a successful removal. The separated product is then checked for purity (purify on column chromatography if needed); its mass is measured to calculate the amount of free base Lidocaine required for the reaction. The estimated mass of Lidocaine in dichloromethane is mixed with 2,4-dinitrocarvacrol, and excess diluent is evaporated using a vacuum evaporator. The obtained red viscous liquid is the final product and the subject of this patent.

Schematic Diagram of Synthesis Procedure

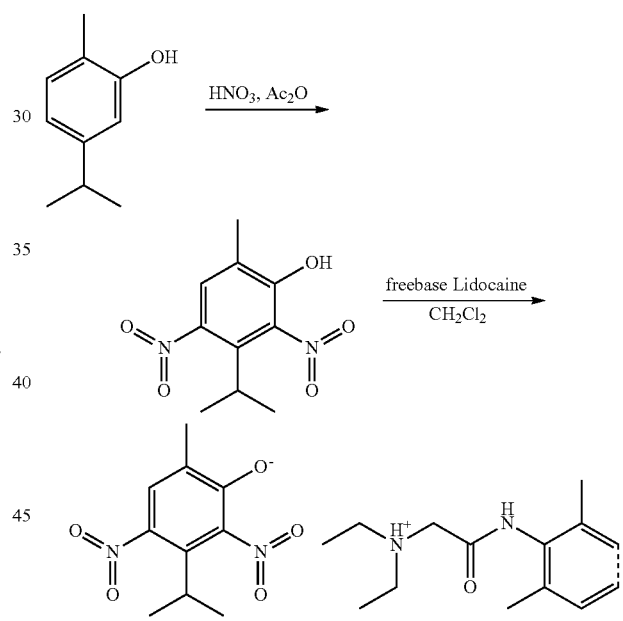

Structural Formula of the Compound

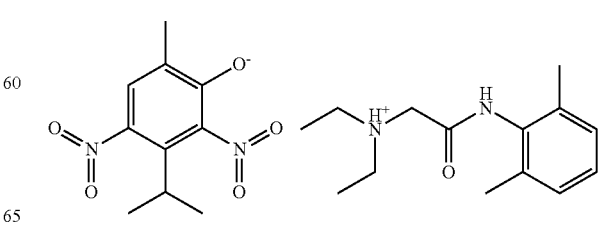

Formula I

Chemical formula: $C_{24}H_{34}N_2O_5$
Molecular mass: 474.46 g mol-1
Compound chemical name: 2,4-dinitro-5-isopropyl-2-methylphenoxy-N-(2,6-dimethylphenylium)-N2,N2-diethylglycinamide Characterization We used 1H-NMR, 13C-NMR and IR spectroscopy for the characterization of our product. In addition, we used Gas chromatography-mass spectrometry (GC-MS) chromatography to check the purity and peak position of our product in given parameters.

BRIEF DESCRIPTION OF THE DRAWINGS

For a more complete understanding of the invention, reference is made to the following description and accompanying drawings, in which:

FIG. 1 1H-NMR spectrum of 2,4-dinitrocarvacrol, obtained after the synthesis of the novel compound;

FIG. 2 1H-NMR spectrum of 2,4-dinitrocarvacrol, obtained after the synthesis of the novel compound;

FIG. 3 13C-NMR spectrum of 2,4-dinitrocarvacrol, obtained after the synthesis of the novel compound;

FIG. 4 1H-NMR spectrum of the novel compound, obtained after it's synthesis;

FIG. 5 13C-NMR spectrum of the novel compound, obtained after it's synthesis;

FIG. 6 IR spectrum of the novel compound, obtained after it's synthesis; and

FIG. 7 Gas chromatography of the novel compound, obtained after it's synthesis.

QUALITY CONTROL

The product is a dark red viscous liquid which is slightly soluble in water, and even more soluble in alkaline solutions. On chromatographie separation, two separate peaks of Lidocaine in cationic form and 2,4-dinitrocarvacrol in anionic form can be seen. Methanol is used as a mobile phase and the peak of Lidocaine becomes available at about 24 min and the peak of 2,4-dinitrocarvacrol at about 26 min. Other possible peaks, if present, could be mononitration products and unreacted Carvacrol, which means that the reaction was not completed. Both mononitrocarvacrol and Carvacrol are considered non-harmless impurities.

Method of Novelty

Since organic salt of 2,4-dinitrocarvacrol with Lidocaine freebase is synthesized for the first time, this product is considered novel. The peaks attributed to Lidocaine and 2,4-dinitrocarvacrol from the 1H-NMR and 13C-NMR spectra prove the product's novelty. The IR spectrum has an area between 2500 cm-1 to 3500 cm-1 that is characteristic for a 2,4-dinitrocarvacrol component of our product and an area from about 1700 cm-1 to 500 cm-1 that has characteristic positions for Lidocaine. That would mean our IR spectrum represents the fingerprint of our novel product.

The novel product's solubility in water is improved by adding nitro groups to its aromatic ring. It can be visually tracked by examining the color of the solution. The nitro group is a well-known chromophore, which means that it changes the ab-sorption of electromagnetic radiation from UV to visible spectra. The nitro groups are also electron-withdrawing by inductive and resonance effects, which improves the acidity of phenolic protons. Improved acidity means that more acidic protons can more easily react with bases. The remaining anion is more stable in solutions of the same pH value than in the case of less acidic ones. The solubility in PSB (phosphate-buffered saline, isotonic solution, and pH of 7.4) is also improved in comparison to Carvacrol salt with Lidocaine because nitrated Carvacrol is a stronger acid than Carvacrol alone, and it tends to make salts with organic bases more efficiently at lower PH levels.

Carvacrol and its derivatives are phenolic compounds, and they are well known for their aggressiveness to pathogens such as bacteria, fungus, etc. The phenolic group is a carrier of that activity, and that group is kept in the transformations, improving its reactivity and making the whole molecule more lyophilic by adding nitro groups. Lidocaine is added for two reasons. The first being, as an organic base, to make a salt: with nitro derivate of Carvacrol, and the second as a local anesthetic because phenolic compound is reactive to tissue and can produce pain on the area of application.

Manufacturing the Compound

This text is a brief description of how the compound will be manufactured.

| | | Formula |
|---|---|---|
| Saline solution: | 99.1 mL | |
| Novel active compound: | 0.9 mL | |
| TOTAL: | 100 mL | |

The compound was obtained by mixing the above stated ingredients in a vacuum mixer (Silverson L5M-A Sealed Unit Lab Mixer) at 6,000 rpm for 20 min.

The Compound In Vitro Test

Here are the findings of the comparative examination of selected pathogens against the novel compound and the antibiotics Cephalosporin and Ampicillin:

| Bacteria | Method | Novel Compound | R | Cephalosporin | R | Ampicilin | R |
|---|---|---|---|---|---|---|---|
| Staphylococcus aureus | Müler-Hinton-Agar | 27 mm | ES | 11 mm | S | 0 mm | R |
| Escherichia coli O157:H7 | Müler-Hinton-Agar | 24 mm | ES | 10 mm | S | 7 mm | MS |
| Salmonella typhimurium DT104 | Müler-Hinton-Agar | 25 mm | ES | 11 mm | S | 6 mm | MS |
| Streptococcus pneumoniae | Müler-Hinton-Agar | 31 mm | ES | 12 mm | S | 0 mm | R |
| Streptococcus pyogenes | Müler-Hinton-Agar | 29 mm | ES | 9 mm | MS | 3 mm | R |
| Streptococcus uberis | Müler-Hinton-Agar | 32 mm | ES | 13 mm | S | 0 mm | R |
| Listeria monocytogenes | Müler-Hinton-Agar | 33 mm | ES | 16 mm | VS | 7 mm | MS |

Amount used: The novel compound 0.05 mL; Cephalosporin 0.1 mL; Ampicillin 0.2 mL.

Evaluation of the results by zone diameter:
- 0 mm to 4 mm: resistant: R
- 5 mm to 9 mm: moderately sensitive: MS
- 10 mm to 15 mm: sensitive: S
- 16 mm to 20 mm: very sensitive: VS
- 21 mm and more: extremely sensitive: ES Testing the Toxicity of the Novel Compound This testing's objective was to determine the acute toxicity—LD50 of the novel compound in mice and rats. Both mice and rats were specially selected for the testing of the toxicity of the compounds, medicine, and chemicals. Only the testing of acute toxicity was done since the active therapy with the novel compound takes from one (1) to three (3) days. Sub-acute toxicity was not necessary and applicable since extended treatment with the novel compound will not be in function or planned. Groups of one hundred (100) lab mice and rats of both genders were placed into glass compartments. They were regularly consuming food manufactured for these lab animals. Water consumption was always available.

In this toxicology test—acute toxicity of the novel compound was tested:
- Oral LD50 p.o.—mice
- Oral LD50 p.o.—rats
- Intraperitoneal LD50—mice
- Intraperitoneal LD50—rats Peroral Application (p.o.) of the Novel Compound—LD50—Testing and Doses The peroral application (p.o.) acute toxicity LD50 testing was done using the standard procedure: application p.o. with the special lab pipette easy to administer liquid product: orally to the lab animals.

Results of the peroral application (p.o.) testing of LD50 of the novel compound on mice:

Peroral application (p.o.) of the novel compound testing LD50 has been on mice: 1 µL/kg, 5 µL/kg, 10 µL/kg, 20 µL/kg, 50 µL/kg, 100 µL/kg, 150 µL/kg, 250 µL/kg, 350 µL/kg, 450 µL/kg, 550 µL/kg, 650 µL/kg, 750 µL/kg, 850 µL/kg, 950 µL/kg, 1,100 µL/kg, 1,250 µL/kg, 1,550 µL/kg, 1,750 µL/kg, and 2,000 µL/kg. At the level of oral dose LD50 2,000 µL/kg—twenty-three (23) mice out of one hundred (100), have changed their behavior and demonstrated light discomfort, running as well as anxiety. Breathing and cardiac functions were regular, function of thorax was regular and without visual changes. Discomfort symptoms were noticed after the applications, disappeared after 1-3 min, diverse from mouse to mouse. No mouse has ended lethally during this test. Conclusion based on these test results was: the novel compound has oral LD50 over 2,000 µL/kg for mice (p.o.). The novel compound is low toxic in the applied doses for mice orally (p.o.).

Results of the peroral application (p.o.) testing of LD50 of the novel compound on rats:

Peroral application (p.o.) of the novel compound testing LD50 has been on rats: 1 µL/kg, 5 µL/kg, 10 µL/kg, 20 µL/kg, 50 µL/kg, 100 µL/kg, 150 µL/kg, 250 µL/kg, 350 µL/kg, 450 µL/kg, 550 µL/kg, 650 µL/kg, 750 µL/kg, 850 µL/kg, 950 µL/kg, 1,100 µL/kg, 1,250 µL/kg, 1,550 µL/kg, 1,750 µL/kg, 2,000 µL/kg, and 2,250 µL/kg. At the level of oral dose LD50 2,250 µL/kg—thirty-seven (37) rats out of one hundred (100), have changed their behavior and demonstrated light discomfort: running over the glass cubical, as well as anxiety. Breathing and cardiac functions were regular, function of thorax was regular and without visual changes. Discomfort symptoms noticed after the applications, disappeared after 1-3 min, diverse from rat to rat. No rat has ended lethally during this test. Conclusion based on these test results was: the novel compound has oral LD50 over 2,250 µL/kg for rats (p.o.). The novel compound is low toxic in the applied doses for rats orally (p.o.).

Intraperitoneal (i.p.) Injection of the Novel Compound—LD50-Testing and Doses

Intraperitoneal testing of the compound LD50 i.e. by pharmaceutical lab needle and syringe, designed for the easy application to the lab animals intraperitoneally.

Results of Intraperitoneal (i.p.) Injection Testing of LD50 of the Novel Compound on Mice:

Intraperitoneal application the novel compound testing LD50 has been on mice: 1 µL/kg, 5 µL/kg, 10 µL/kg, 20 µL/kg, 50 µL/kg, 100 µL/kg, 150 µL/kg, 250 µL/kg, 350 µL/kg, 450 µL/kg, 550 µL/kg, 650 µL/kg, 750 µL/kg, 850 µL/kg, 950 µL/kg, 1,100 µL/kg, 1,250 µL/kg, and 1,550 µL/kg. At the level of i.p. dose LD50 1,550 µL/kg—twenty-one (21) mice out of one hundred (100), have changed their behavior and demonstrated discomfort: running as well as anxiety. Breathing and cardiac functions were regular, function of thorax was regular and without visual changes. Discomfort symptoms noticed after the applications, disappeared after 3-5 min, diverse from mouse to mouse. No mouse has ended lethally during this test. Conclusion based on these test results was that the novel compound's Intraperitoneal application has LD50 over 1,550 µL/kg for mice. The novel compound is low toxic in the applied doses on mice.

Results of Intraperitoneal (i.p.) Injection Testing of LD50 of the Novel Compound on Rats:

Intraperitoneal application of the novel compound testing LD50 has been on rats: 1 µL/kg, 5 µL/kg, 10 µL/kg, 20 µL/kg, 50 µL/kg, 100 µL/kg, 150 µL/kg, 250 µL/kg, 350 µL/kg, 450 µL/kg, 550 µL/kg, 650 µL/kg, 750 µL/kg, 850 µL/kg, 950 µL/kg, 1,100 µL/kg, 1,250 µL/kg, 1,550 µL/kg, and 1,750 µL/kg. At the level of i.p. dose LD50 1,750 µL/kg—twenty-nine (29) rats out of one hundred (100), have changed their behavior and demonstrated discomfort: running over the glass cubical as well as the anxiety. Breathing and cardiac functions were regular, function of thorax was regular and without visual changes. Discomfort symptoms noticed after the applications, disappeared after 5-6 min, diverse from rat to rat. No rat has passed lethally during this test. Conclusion based on these test results was: the novel compound's Intraperitoneal application has LD50 over 1,750 ML/kg for rats. The novel compound is low toxic in the applied doses on rats.

What is claimed:

1. A method for synthesizing a compound having a structure of the following formula I:

Formula I

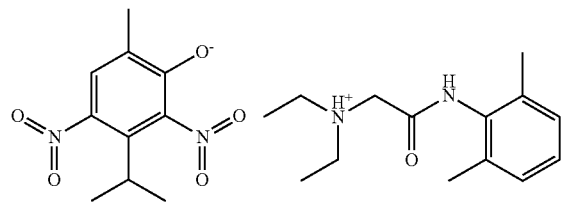

by reacting Carvacrol and Lidocaine to produce said compound.

2. The compound having the structure of the following formula I:

Formula I

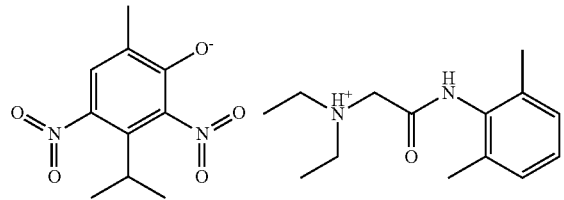

produced by the method of claim 1.

3. A liquid formulation for IV therapy, wherein the liquid formulation comprises the compound of claim 2.

4. A method for treating bacterial infections in humans caused by pathogens resistant to antibiotics, wherein said bacterial infections are caused by a bacteria selected from the group consisting of Methicillin-resistant *Staphylococcus aureus* (MRSA), *Streptococcus faecalis, Mycobacterium tuberculosis, Escherichia* spp. *E. coli, Salmonella* spp. *Pasteurella* spp., *Corynebacterium* spp., *Bacillus* spp., *Bacillusanthracis, Clostridium* spp., *Spherophorus* spp., *Candida* spp., *Trichophyton* spp., *Microsporum* spp., *Mycobacterium* spp., *Vibrio* spp., *Cryptosporidium* spp., *Microsporidia* spp., *Listeria monocytogenes, Lawsonia intracellularis, Treponema dysenteriae, Enterococcus* spp., *Haemophilus* spp., *Campylobacter* spp., *Chlamydia* spp., or *Brucella* spp.

* * * * *